United States Patent
Okazaki et al.

(10) Patent No.: US 9,860,969 B2
(45) Date of Patent: Jan. 2, 2018

(54) RADIO FREQUENCY VOLTAGE CONTROL SYSTEM IN SYNCHROTRON ACCELERATING CAVITY

(71) Applicant: Hitachi, Ltd., Tokyo (JP)

(72) Inventors: Kimiko Okazaki, Tokyo (JP); Hideaki Nishiuchi, Tokyo (JP); Kunio Moriyama, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 91 days.

(21) Appl. No.: 14/679,047

(22) Filed: Apr. 6, 2015

(65) Prior Publication Data
US 2015/0283404 A1 Oct. 8, 2015

(30) Foreign Application Priority Data

Apr. 7, 2014 (JP) ................................ 2014-078544

(51) Int. Cl.
*H05H 13/04* (2006.01)
*A61N 5/10* (2006.01)

(52) U.S. Cl.
CPC ........... *H05H 13/04* (2013.01); *A61N 5/1077* (2013.01); *A61N 5/1048* (2013.01); *A61N 2005/1087* (2013.01)

(58) Field of Classification Search
CPC .. A61N 5/1077; A61N 5/1067; A61N 5/1048; A61N 2005/1074; A61N 5/1031; G21K 1/08; H05H 13/04; H05H 2007/004; H05H 7/12; H05H 2007/122; H05H 7/02; H05H 2007/025; A61B 2018/00636; A61B 6/4092
See application file for complete search history.

(56) References Cited

U.S. PATENT DOCUMENTS

| 8,878,432 B2 * | 11/2014 | Chen .................... A61N 5/1048 |
| | | 315/5.41 |
| 9,167,681 B2 * | 10/2015 | Cheung .................... H05H 7/02 |
| 9,215,791 B2 * | 12/2015 | Arita ........................ H05H 7/04 |
| 9,456,487 B2 * | 9/2016 | Takase .................... H05H 7/02 |

(Continued)

FOREIGN PATENT DOCUMENTS

WO    WO2014/016896    *   1/2014   ............... H05H 7/02

OTHER PUBLICATIONS

Takuji Furukawa et al., Fast beam cut-off method in RF-knockout extraction for spot-scanning, Nuclear Instruments & Methods in Physics Research A 489 (2002) 59-67.

*Primary Examiner* — Brooke Purinton
(74) *Attorney, Agent, or Firm* — Mattingly & Malur, PC

(57) ABSTRACT

At the start of beam extraction, the amplitude value of an acceleration radio frequency voltage is held at a first amplitude value. When the irradiation dose stemming from beam extraction reaches a prescribed dose, the amplitude value of the acceleration radio frequency voltage applied to an accelerating cavity starts to be increased from the first amplitude value to a second amplitude value. When the irradiation dose reaches a target dose, the amplitude value is raised to and held at the second amplitude value. By the time the irradiation is restarted, the amplitude value of the acceleration radio frequency voltage applied to the accelerating cavity is reduced from the second amplitude value to the first amplitude value. At the start of beam extraction, the amplitude value is held at the first amplitude value.

5 Claims, 5 Drawing Sheets

(56) References Cited

U.S. PATENT DOCUMENTS

| | | | |
|---|---|---|---|
| 2011/0266981 A1* | 11/2011 | Umezawa | G21K 1/093 315/506 |
| 2014/0152199 A1* | 6/2014 | Arita | H05H 7/04 315/503 |
| 2014/0187844 A1* | 7/2014 | Saito | A61N 5/1077 600/1 |

* cited by examiner

PRIOR ART

RADIO FREQUENCY VOLTAGE CONTROL SYSTEM IN SYNCHROTRON ACCELERATING CAVITY

BACKGROUND OF THE INVENTION

The present invention relates to a charged particle beam irradiation system as part of a particle beam treatment system and an operating method for the charged particle beam irradiation system. More particularly, the invention relates to a charged particle beam irradiation system adapted to a particle beam treatment system for irradiating a cancer tumor with a charged particle beam (ion beam) of protons or carbon ions for treatment, and an operating method for the charged particle beam irradiation system.

In recent years, the rate of cancer incidence has been rising. With this trend has come progress in various methods for cancer treatment. Particle beam treatment is one method of radiation treatment involving irradiation of the cancer tumor with an accelerated charged beam particle such as a proton beam or a carbon ion beam for the destruction of cancer cell DNA. This method has been attracting attention in recent years because it is a minimally invasive technique that is less stressful on the body and permits higher quality of life after treatment.

The particle beam treatment system is made up of a charged particle beam generator, a high-energy beam transport system, an irradiation device, and a control device for controlling these components.

What is drawing attention in connection with the particle beam treatment system is the scanning irradiation method which, when an irradiation device irradiates a tumor with a charged particle beam in keeping with the tumor shape, involves causing the tumor to be irradiated with the beam through scanning by use of magnets.

According to the scanning irradiation method, the target tumor is divided into scanning regions called layers in the depth direction under the body surface. The plane of each layer is further divided into dose-controlled regions called spots. In this state, each layer plane is scanned with the charged particle beam for irradiation with the dose suitably controlled for each spot. A change from one irradiation plane to another is accomplished by varying the energy of the charged particle beam for irradiation.

Specifically, the value of the current for the scanning magnet is set. When a target spot is reached, that spot is irradiated with a set dose. When the irradiation dose has reached the set value, the next spot is reached. When the movement to the next irradiation position is completed, the charged particle beam is again extracted. Extraction and deactivation of the charged particle beam are repeated until the irradiation within one layer is finished. When the irradiation of one layer is completed, the beam energy is changed for the next layer, and the irradiation is repeated likewise. This is the so-called spot scanning method in which the charged particle beam for irradiation is turned off during movement from one irradiation spot to another.

The spot scanning method permits irradiation with the charged particle beam in keeping with the tumor shape and eliminates the need for patient-specific instruments such as the bolus and collimator required traditionally for the scatterer irradiation method. This makes it possible efficiently to irradiate the tumor with the charged particle beam supplied from the charged particle beam generator to the irradiation device.

Synchrotrons are used extensively as the charged particle beam generator for the particle beam treatment system. The radio frequency beam extraction method is one known method for extracting the beam from the synchrotron to the irradiation device.

The radio frequency beam extraction method involves increasing the amplitude of betatron vibrations of an orbiting charged particle beam by application of an extraction radio frequency voltage for extraction starting with particles having amplitudes exceeding a stability limit condition.

The extraction method above allows the set value of the magnet making up the synchrotron to be set constant during extraction. For this reason, the radio frequency beam extraction method offers enhanced orbiting stability of the extracted charged particle beam and provides highly accurate control of the position irradiated therewith. Also, because the extraction radio frequency voltage is turned off at the end of the irradiation of each spot, it is easy to stop the charged particle beam (e.g., see Nuclear Instruments and Method in Physics Research, A 489 (2002), pp. 59-67).

SUMMARY OF THE INVENTION

However, from the time the extraction radio frequency voltage is turned off until the extracted charged particle beam is actually cut off, there elapses a time period corresponding to the synchrotron oscillation period of the orbiting charged particle beam. Thus there has been a need for ways to shorten a stop time in which the charged particle beam is to be stopped.

Since the charged particle beam stop time is stipulated by synchrotron oscillation, shortening the charged particle beam stop time requires increasing the synchrotron oscillation. To increase the synchrotron oscillation in turn requires boosting the acceleration radio frequency voltage. However, if the acceleration radio frequency voltage is constantly elevated during beam extraction, a charged particle beam having a large momentum dispersion is extracted first. This can cause large fluctuations of the range of the charged particle beam. It is thus feared that the dose of the charged particle beam could be diverted from its target value.

The present invention has been made in view of the above circumstances and provides a charged particle beam irradiation system and an operating method for that system which shortens the stop time of the extracted charged particle beam while suppressing the momentum dispersion of the charged particle beam.

In carrying out the present invention and according to one embodiment thereof, there is provided a charged particle beam irradiation system including: a synchrotron accelerating a charged particle beam and having the accelerated charged particle beam extracted therefrom; an irradiation device performing irradiation with the charged particle beam extracted from the synchrotron; a beam transportation system guiding the charged particle beam from the synchrotron to the irradiation device; and a controller controlling the synchrotron, the beam transportation system, and the irradiation device. The synchrotron has an accelerating cavity accelerating the charged particle beam with a radio frequency acceleration voltage up to a predetermined energy level. The controller has an acceleration radio frequency controller configured to control a radio frequency voltage to be applied to the accelerating cavity, the acceleration radio frequency controller being operable to increase the amplitude value of the radio frequency voltage applied to the accelerating cavity when an irradiation dose of the charged particle beam reaches a prescribed dose and to reduce the increased amplitude value of the radio frequency voltage by the time the irradiation with the charged particle beam is restarted.

According to the present invention, it is possible to shorten the stop time in which the extraction of the charged particle beam is to be stopped while suppressing the momentum dispersion of the charged particle beam.

DESCRIPTION OF THE PREFERRED EMBODIMENTS

A charged particle beam irradiation system embodying the present invention and an operating method for the system will now be explained with reference to FIGS. 1 through 5.

Figure 1:
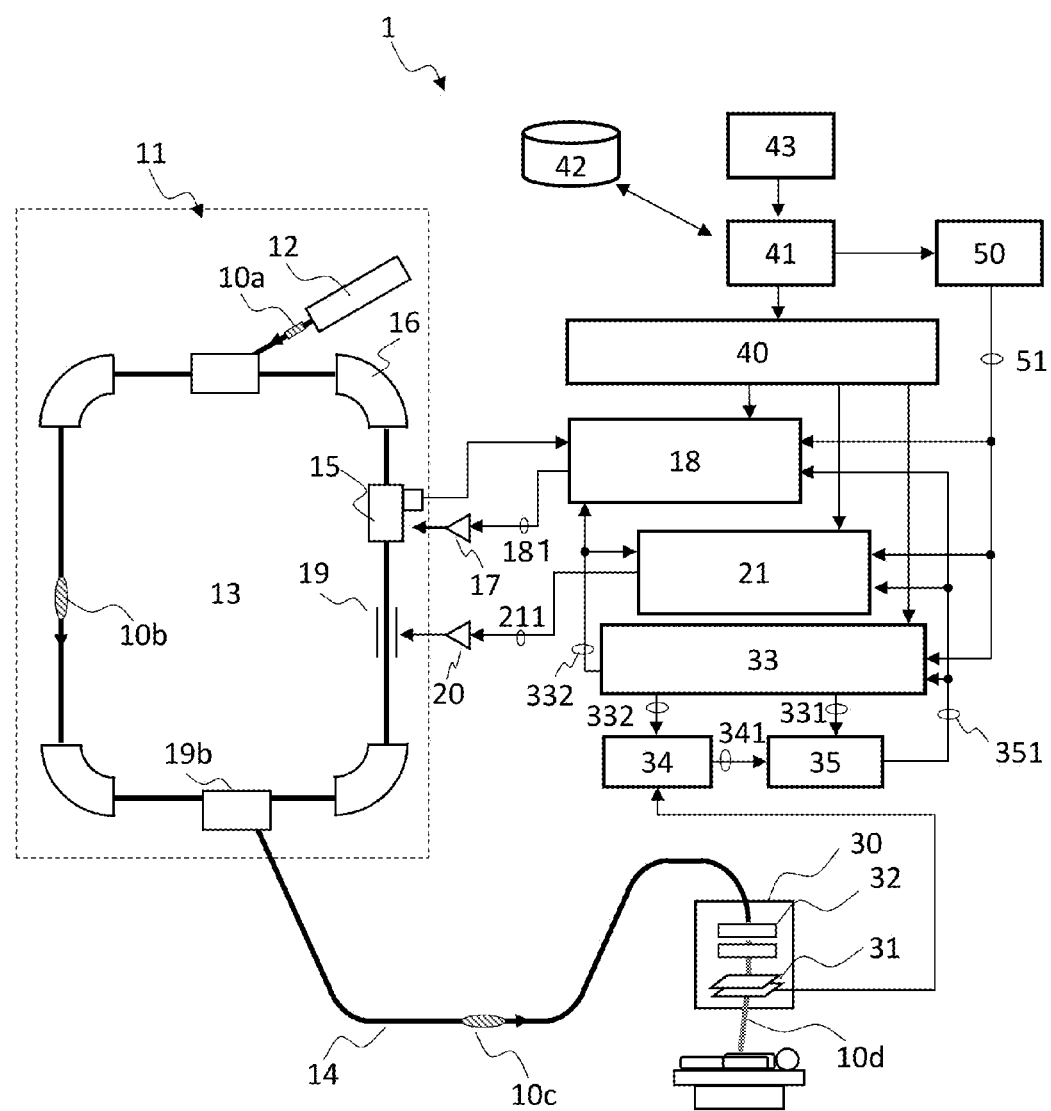
FIG. 1 is a diagram showing a typical configuration of a particle beam treatment system.
Figure 2:
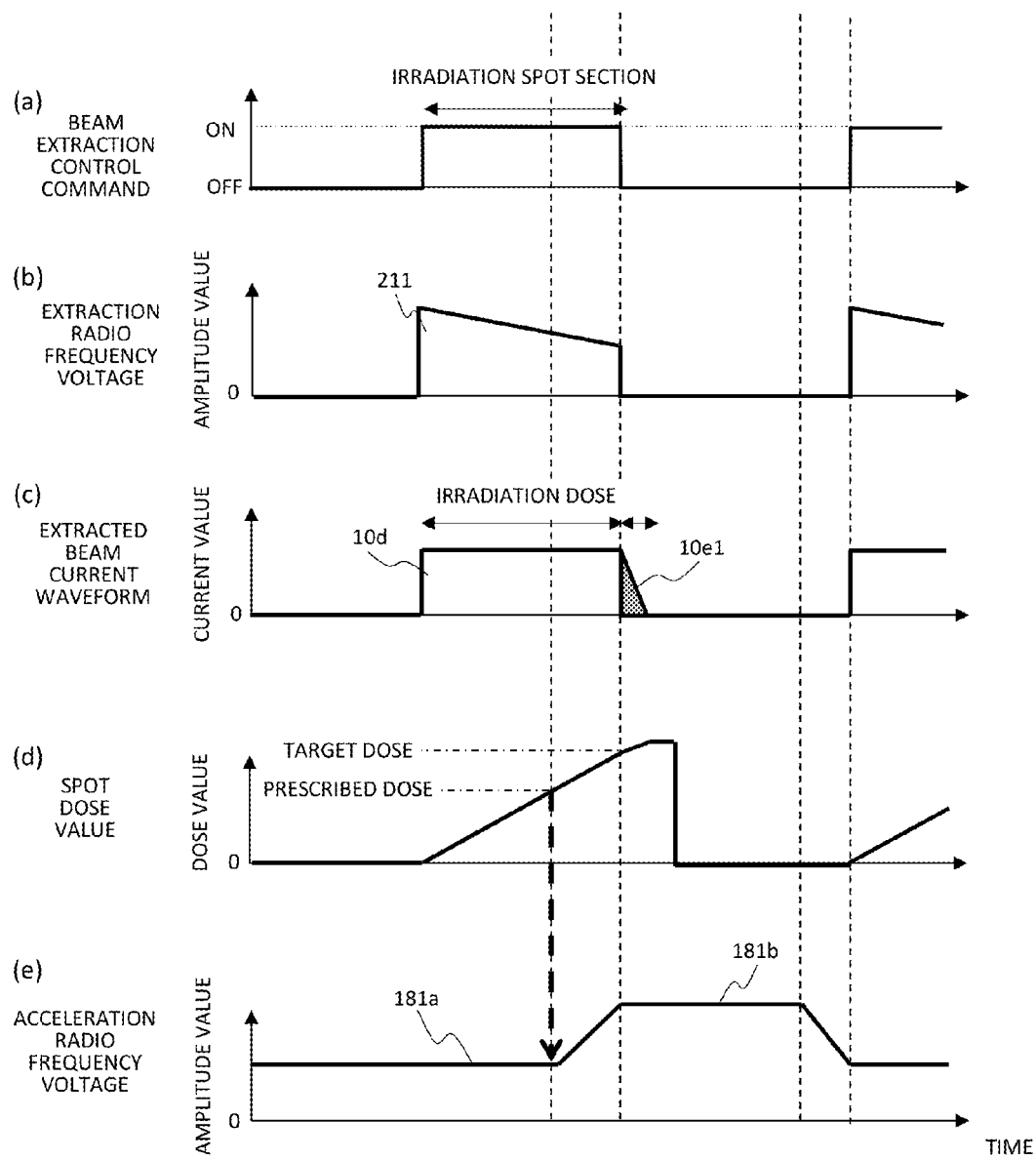
FIG. 2 is a waveform chart showing typical current waveforms of an extracted charged particle beam of a charged particle beam irradiation system as one embodiment of the present invention.
Figure 3:
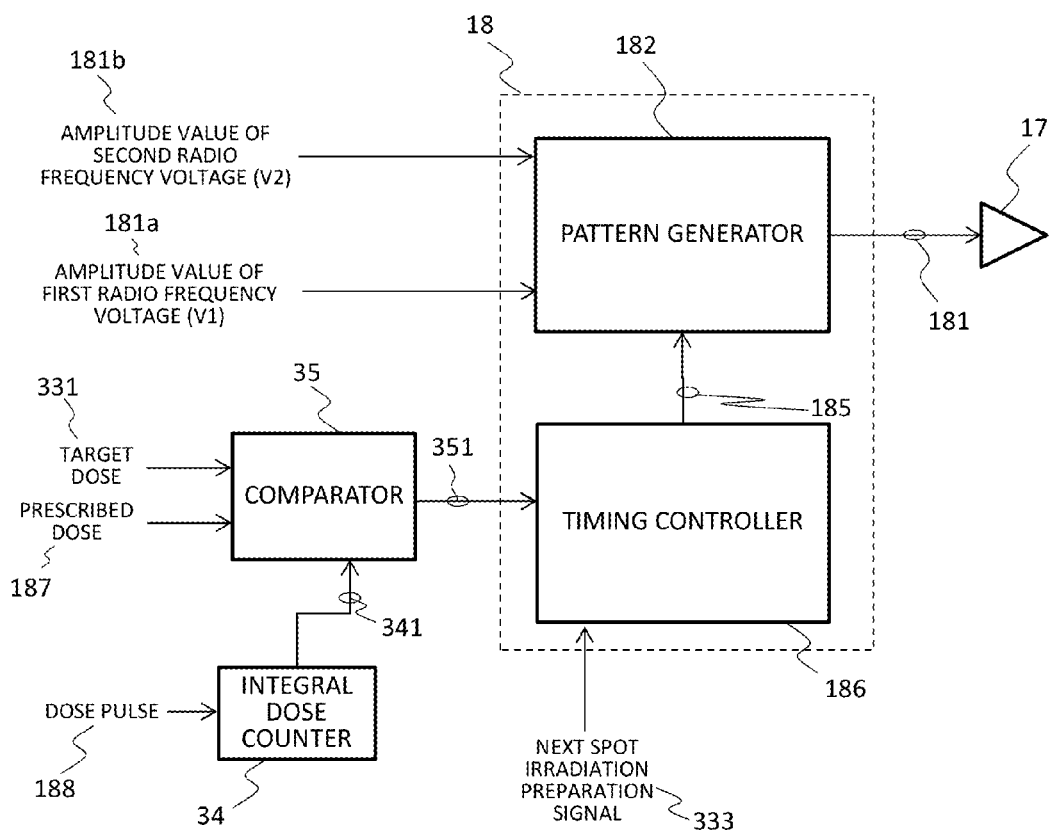
FIG. 3 is a diagram showing a typical configuration of an acceleration controller and its peripheral devices, the acceleration controller performing timing control of an acceleration radio frequency voltage of the charged particle beam irradiation system embodying the invention.
Figure 4:
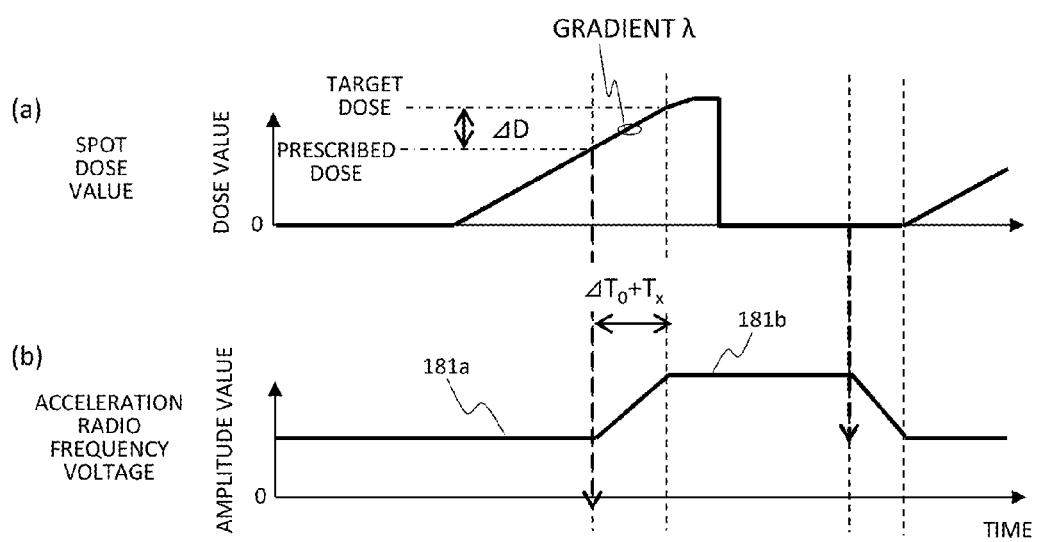
FIG. 4 is a waveform chart showing an example in which to determine the timings for increasing and decreasing the amplitude value of the acceleration radio frequency voltage of the charged particle beam irradiation system embodying the invention.
Figure 5:
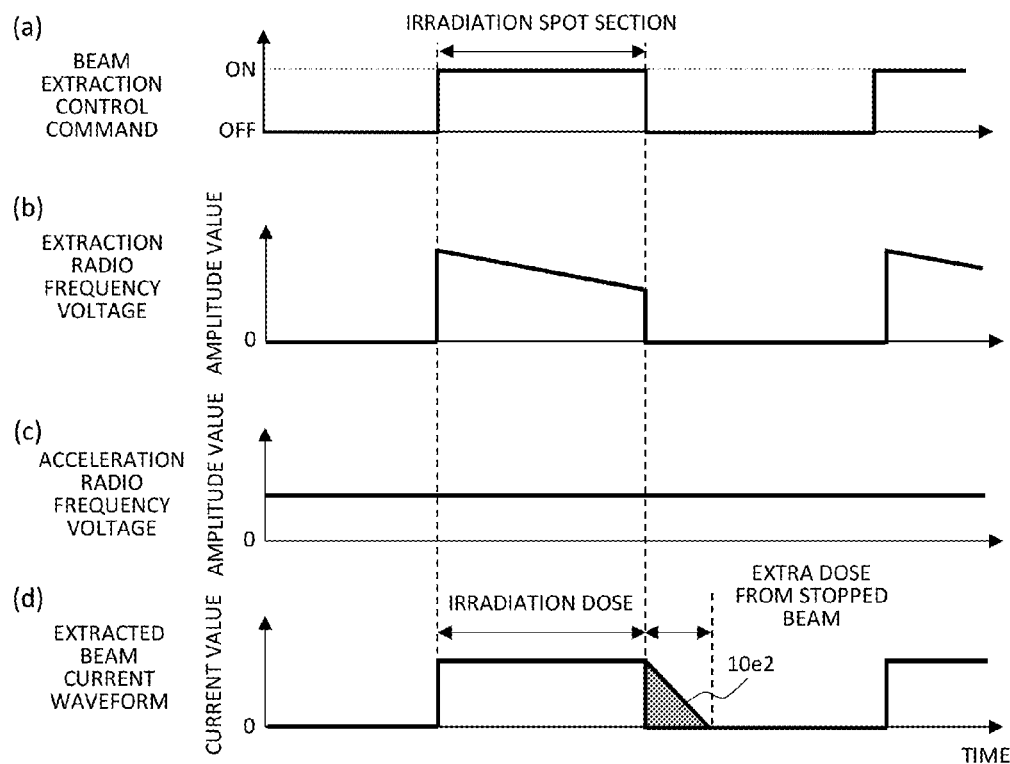
FIG. 5 is a waveform chart showing typical current waveforms of the extracted charged particle beam of the prior art.

FIG. 1 is a diagram showing a typical configuration of a particle beam treatment system. FIG. 2 is a waveform chart showing typical current waveforms of an extracted charged particle beam of the charged particle beam irradiation system as one embodiment of the present invention. FIG. 3 is a diagram showing a typical configuration of an acceleration controller and its peripheral devices, the acceleration controller performing timing control of an acceleration radio frequency voltage of the charged particle beam irradiation system embodying the invention. FIG. 4 is a waveform chart showing an example in which to determine the start timings for increasing and decreasing the amplitude value of the acceleration radio frequency voltage of the charged particle beam irradiation system embodying the invention. FIG. 5 is a waveform chart showing typical current waveforms of the extracted charged particle beam of the prior art.

As shown in FIG. 1, a particle beam treatment system 1 of this embodiment includes a charged particle beam generator 11, a high-energy beam transportation system 14, an irradiation device 30, and a control system.

The charged particle beam generator 11 includes a charged particle source (not shown), an injector 12, and a synchrotron 13. The charged particle source is connected to the injector 12. The injector 12 is in turn connected to the synchrotron 13. The injector 12 accelerates a charged particle beam generated by the charged particle source up to an energy level high enough to inject the generated charged particle beam into the synchrotron 13. The charged particle beam 10a accelerated by the injector 12 is injected into the synchrotron 13.

The synchrotron 13 includes a radio frequency accelerator (accelerating cavity) 15 that applies a radio frequency voltage to the charged particle beam 10b circulating in orbit for acceleration to a target energy level, a radio frequency extraction electrode 19 that increases the betatron oscillation amplitude of the orbiting charged particle beam, an extraction deflector 19b for extracting the charged particle beam from orbit and a bending magnet 16.

The high-energy beam transportation system 14 connects the charged particle beam generator 11 with the irradiation device 130 installed in the treatment room. The high-energy beam transportation system 14 transports a charged particle beam 10c extracted from the charged particle beam generator 11 to the irradiation device 30.

The irradiation device 30 is made up of a scanning magnet 32 that deflects horizontally and vertically the charged particle beam transported by the beam transportation system 14 to cause an irradiation target to be scanned two-dimensionally in keeping with its cross-sectional shape with the deflected beam, and a dose monitor 31 that monitors the position, size (shape), and dose of the charged particle beam 10d for scanning by the scanning magnet 32.

The control system of the particle beam treatment system 1 includes an accelerator controller 40 that controls the charged particle beam generator 11 and high-energy beam transportation system 14, a main controller 41 that controls the particle beam treatment system 1 as a whole, a treatment planning device 43 that plans charged particle beam irradiation conditions for patients, a data storage device 42 that stores the information planned by the treatment planning device 43 and the control information for the charged particle beam generator 11 and high-energy beam transportation system 14, a timing system 50 that generates and outputs a timing signal 51 for implementing synchronous control of the devices constituting the charged particle beam generator 11, an acceleration controller 18, an extraction controller 21, an irradiation controller 33 that outputs a beam extraction control command 332 for extracting the beam from the synchrotron 13, an integral dose counter 34 that counts the dose monitored by the dose monitor 31, a comparator 35 that compares the count value from the integral dose counter 34 with a target value, and an interlock system (not shown) that ensures the safety of the patent independently of the main controller 41. The extraction controller 21 controls the radio frequency used to extract the charged particle beam from the charged particle beam generator 11 to the high-energy beam transportation system 14. The acceleration controller 18 controls the radio frequency voltage for accelerating the charged particle beam orbiting inside the synchrotron 13.

In the above-mentioned synchrotron 13, an acceleration radio frequency amplifier 17 amplifies an acceleration radio frequency signal 181 to generate a radio frequency voltage and applies the generated radio frequency voltage to the accelerating cavity 15. The charged particle beam 10b thus injected into the synchrotron 13 is energized when passing through the accelerating cavity 15 for acceleration up to a desired energy level. At this point, the magnetic field strengths of the bending magnet 16 and of a quadruple magnet (not shown) etc. and the frequency of the radio frequency voltage applied to the accelerating cavity 15 are raised in keeping with the increase in the orbiting energy of the charged particle beam 10b in the synchrotron so that the orbit of the charged particle beam 10b circulating in the synchrotron 13 will remain constant.

Given the charged particle beam 10b accelerated to the desired energy level, the condition for enabling the orbiting charged particle beam 10b to be extracted (i.e., stability limit condition of the orbiting charged particle beam) is formulated by the amounts of excitation of the quadruple magnet and a hexapole magnet (not shown) under extraction preparation control. After extraction preparation control is confirmed to have ended, an extraction radio frequency amplifier 20 generates an extraction radio frequency voltage by amplifying an extraction radio frequency signal 211 output from the extraction controller 21. Thereafter, the generated extraction radio frequency voltage is applied to the radio frequency extraction electrode 19 in order to increase the betatron oscillation amplitude of the orbiting charged particle beam in the synchrotron 13. The increase in the betatron oscillation amplitude causes the orbiting charged particle beam 10b exceeding the stability limit condition to be extracted from the synchrotron 13 to the high-energy charged particle beam transportation system 14. Extraction of the charged particle beam from the synchrotron 13 may be controlled by the extraction controller 21 turning on and off the extraction radio frequency signal 211 applied to the radio frequency extraction electrode 19. At this point, the acceleration radio frequency voltage applied to the accelerating cavity 15 during beam extraction is kept applied. That is, even when the extraction radio frequency signal is turned off, application of the acceleration radio frequency voltage is not stopped.

The charged particle beam 10c extracted from the synchrotron 13 is transported to the irradiation device 30 by the high-energy beam transportation system 14. The irradiation device 30 verifies successively the dose strength of the charged particle beam 10d applied to the patient by use of the dose monitor 31 for irradiation dose measurement, and scans the tumor in keeping with its shape with the charged particle beam 10d using the scanning magnet 31. The range of the charged particle beam in the depth direction of the patient may be changed by varying the energy of the charged particle beam 10b to be accelerated by the synchrotron 13 for extraction therefrom, so that there may be provided an irradiation boundary conforming to the tumor shape.

What follows is an explanation of how to control synchrotron oscillation, which is important for this embodiment.

As described above, the synchrotron accelerates the charged particle beam using the accelerating cavity 15 installed on the orbit of the beam, the charged particle beam getting energized with the acceleration radio frequency voltage per turn in orbit for acceleration. The energizing with the radio frequency voltage by the accelerating cavity 15 provides a stability region called the radio frequency bucket.

The radio frequency bucket designates a momentum width of the charged particle beam that can orbit stably with regard to the phase of the acceleration radio frequency voltage. The height of the radio frequency bucket is prescribed by the amplitude value of the acceleration radio frequency voltage.

Of the charged particles orbiting in the synchrotron, those whose frequency coincides with that of the acceleration radio frequency voltage match the momentum prescribed by the latter, so that the particles are distributed in the center phase of the acceleration radio frequency voltage. The orbiting particles not coinciding with the frequency of the acceleration radio frequency voltage are diverted relatively from the momentum prescribed by the latter, so that the particles are distributed in regions deviating from the center phase of the radio frequency voltage and orbit in the phase space within the radio frequency bucket. The orbital motion in the phase space within the radio frequency bucket is called synchrotron oscillation. The charged particle beam entailing synchrotron oscillation orbits in the radio frequency bucket; synchrotron oscillation constitutes an important motion for the charged particle beam to be in stable orbit.

The synchrotron oscillation frequency ($f_{SYNC}$) is defined by the expression (1) given below, and is controlled by the acceleration radio frequency voltage ($V_{RF}$), orbiting frequency ($\Omega$), and synchronous phase ($\varphi s$).

$$f_{SYNC} = \frac{\sqrt{-\frac{eV_{RF}}{2\pi}\frac{h\eta\Omega\cos(\phi_s)}{pR}}}{2\pi} \quad (1)$$

The effect of synchrotron oscillation on the charged particle beam orbiting inside the synchrotron is different between the time of acceleration and the time of extraction. The difference is explained below by use of the expression (1) above.

At the time of acceleration of the charged particle beam, the orbital frequency of the charged particle beam orbiting in the synchrotron is increased, and so is the energy (i.e., momentum) of the charged particle beam. At this point, large synchrotron oscillation shortens the oscillation period of the charged particles orbiting in the radio frequency bucket. Thus there is fear that the charged particle beam may be lost because of the increase in momentum by acceleration control and due to fluctuations in momentum caused by synchrotron oscillation. For this reason, it is necessary to ease the fluctuations in the acceleration radio frequency voltage ($V_{RF}$) and in the synchronous phase ($\varphi s$) so as to suppress abrupt changes in synchrotron oscillation.

On the other hand, at the time of extraction of the charged particle beam, the acceleration radio frequency voltage ($V_{RF}$) and synchronous phase ($\Omega s$) are controlled to be constant, so that synchrotron oscillation remains stable. Also, the charged particle beam is extracted from out of the stability limit when the amplitude of betatron oscillation is increased by application of the extraction radio frequency voltage. At this point, the response of the charged particle beam, i.e., the beam ON/OFF response time is dependent on the synchrotron oscillation frequency ($f_{SYNC}$).

Here, it is possible to shorten the ON/OFF response time of the charged particle beam by constantly raising the acceleration radio frequency voltage ($V_{RF}$) during extraction control to increase the synchrotron oscillation frequency ($f_{SYNC}$). However, the orbiting charged particle beam tends to be extracted starting from the charged particles having a high momentum realized by synchrotron oscillation. This tendency can incur the problem of the enhanced acceleration radio frequency voltage ($V_{RF}$) leading to pronounced changes in the momentum of the charged particle beam extracted from the synchrotron.

Under these circumstances, present embodiment takes note of the fact that the charged particle beam stop time is prescribed by synchrotron oscillation. The embodiment thus shortens the charged particle beam stop time by getting the acceleration radio frequency voltage to control synchrotron oscillation when the charged particle beam is stopped, while performing control to reduce the fluctuations in the momentum of the charged particle beam extracted from the synchrotron. The details of the controls will be described below in comparison with the typical prior-art method.

FIG. 5 is a control timing chart of the extracted charged particle beam of the prior art. FIG. 2 is a control timing chart of the radio frequency voltage according to the present invention.

According to the prior art, as shown in FIG. 5, the acceleration radio frequency voltage remains constant when the charged particle beam is stopped as well as when it is extracted. Extraction and deactivation of the charged particle beam are controlled by turning on and off the extraction radio frequency voltage. Thus with the prior art, as discussed above, it takes time after the extraction radio frequency voltage is turned off until the charged particle beam being extracted is actually cut off, the elapsed time being proportional to the synchrotron oscillation period of the orbiting charged particle beam. An extra irradiation beam 10e2 is known to occur when the charged particle beam is stopped as shown in FIG. 5(d).

According to the present invention, as shown FIG. 2, synchrotron oscillation is enhanced by increasing the amplitude value of the acceleration radio frequency voltage when the charged particle beam is stopped. This shortens the charged particle beam stop time. By the time the beam is again extracted, the amplitude value of the acceleration radio frequency voltage is returned to the initial value, so that the momentum dispersion (range fluctuations) in effect when the charged particle beam is extracted is suppressed.

How the control above is implemented is explained below by use of a control block diagram of the acceleration radio frequency voltage in FIG. 3.

In FIG. 3, the acceleration controller 18 includes a pattern generator 182 and a timing controller 186. The pattern generator 182 generates a voltage pattern in which the amplitude value of the acceleration radio frequency voltage is raised from a first amplitude value 181a (V1) to a second amplitude value 181b (V2) when the charged particle beam passing through the dose monitor 31 reaches a prescribed dose. Also, the pattern generator 182 generates a voltage pattern in which the amplitude value of the acceleration radio frequency voltage is lowered from the second amplitude value V2 to the first amplitude value V1 by the time irradiation is resumed. The timing controller 186 controls the pattern generation timing of the acceleration radio frequency voltage ($V_{RF}$).

The timing controller 186 generates a pattern generation timing signal 185 based on the substance of a comparator output signal 351 output from the comparator 35 and on a target dose 331 and a prescribed dose 187 output from the accelerator controller 40. The timing controller 186 outputs the pattern generation timing signal 185 thus generated to the pattern generator 182.

In accordance with the substance of the pattern generation timing signal 185, the pattern generator 182 generates a voltage pattern in which the amplitude value of the acceleration radio frequency voltage applied to the accelerating cavity 15 is raised from V1 to V2 and also a voltage pattern in which the amplitude value is reduced from V2 to V1. The pattern generator 182 outputs the generated voltages patterns to the acceleration radio frequency amplifier 17 as the acceleration radio frequency signal 181. Thereafter, the acceleration radio frequency signal 181 is amplified by the acceleration radio frequency amplifier 17, with the radio frequency voltage applied to the accelerating cavity 15.

In FIG. 3, the integral dose counter 34 cleared to zero at the start of spot irradiation counts up dose pulses 188 output from the dose monitor 31. The integral dose counter 34 outputs the resulting count value 341 to the comparator 35. The comparator 35 compares the count value 341 from the integral dose counter 34 with the target dose 331 and prescribed dose 187 output from the accelerator controller 40 and predetermined per spot. When the count value 341 reaches the prescribed dose 187, the comparator 35 outputs the comparator output signal 351 notifying the timing controller 186 in the acceleration controller 18 that the prescribed dose has been reached. When receiving the input of this signal, the timing controller 186 outputs to the pattern generator 182 the pattern generation timing signal 185 for generating the voltage pattern in which the acceleration radio frequency voltage is raised from V1 to V2 until the count value 341 reaches the target dose 331. When receiving the input of this signal, the pattern generator 182 generates the voltage pattern in which the acceleration radio frequency voltage is raised from V1 to V2, and outputs the generated voltage pattern to the acceleration radio frequency amplifier 17. The amplitude-increasing voltage pattern is not limited to the linear increase pattern such as one shown in FIG. 2 (e). The voltage pattern may also be one of a chronologically consecutive increase or one of a stepped increase.

An example showing how to determine the prescribed dose 187 is explained below with reference to FIG. 4.

In FIG. 4, a dose rate λ is defined as the dose increased per unit time of the charged particle beam extracted from the synchrotron 13 and applied by the irradiation device 30. Because the dose rate λ can be controlled by use of the strength of the extraction radio frequency voltage, the dose rate λ is a predetermined parameter.

If it is assumed that $\Delta T_0$ is the time period required to raise the amplitude value of the acceleration radio frequency voltage from the first amplitude value 181a (V1) to the second amplitude value 181b (V2) and that ΔD is the dose value raised during the time period $\Delta T_0$, then the following expression is obtained:

$$\Delta T_0 = \Delta D / \lambda \qquad (2)$$

The expression (2) above may be transformed into the following:

$$\lambda \Delta T_0 = \Delta D = \text{target dose} - \text{prescribed dose} \qquad (3)$$

Therefore, the prescribed dose may be defined by the following expression (4):

$$\text{Prescribed dose} = \text{target dose} - \lambda \Delta T_0 \qquad (4)$$

The expression (4) may be supplemented with an extra time $T_X$ to ensure sufficient room for the amplitude value of the acceleration radio frequency voltage to reach V2 unfailingly. Thus the prescribed dose should preferably be defined by the following expression (5):

$$\text{Prescribed dose} = \text{target dose} - \lambda(\Delta T_0 + T_X) \qquad (5)$$

Likewise, when the count value 341 has reached the target dose 331, the comparator 35 outputs a target dose reaching timing signal to the irradiation controller 33. On the basis of this signal output from the comparator 35, the irradiation controller 33 outputs an OFF command to turn off the beam extraction control command 332. This causes the extraction controller 21 to turn off the extraction radio frequency voltage.

If the amplitude value of the acceleration radio frequency voltage is kept raised, the height of the radio frequency bucket at the time of extraction of the charged particle beam is elevated, so that the momentum dispersion of the orbiting charged particle beam expands along the height of the radio frequency bucket. This in turn causes the momentum dispersion (range fluctuations) of the extracted charged particle beam gradually to increase. Thus the method above may not be capable of meeting predetermined performance of the extracted charged particle beam.

The timing controller 186 receives the input of a next spot irradiation preparation signal 333 indicating that the current value of the scanning magnet 32 has reached a target current value for irradiation of the next spot and that a high-speed steering magnet (not shown) inside the beam transportation system 14 is turned off. At the time of receiving this next spot irradiation preparation signal 333, the timing controller 186 outputs to the pattern generator 182 the pattern generation timing signal 185 for generating the voltage pattern in which to lower the acceleration radio frequency voltage from V2 to V1. Given the input of this signal, the pattern generator 182 generates the voltage pattern in which to reduce the amplitude value of the acceleration radio frequency voltage from V2 to V1 and outputs the thus generated voltage pattern to the acceleration frequency amplifier 17. When it is determined that the amplitude value of the acceleration radio frequency voltage has reached V1, the irradiation controller 33 performs control to start irradiation of the next spot. The amplitude-reducing voltage pattern is also not limited to the linear decrease pattern such as one shown in FIG. 2(*e*). Alternatively, the voltage pattern may be one of a chronologically consecutive decrease or one of a stepped decrease.

According to the present invention, when the timing controller 186 and pattern generator 182 in the acceleration controller 18 generate the patterns and send them to the acceleration radio frequency amplifier 17 as explained above, the amplitude value of the acceleration radio frequency voltage applied to the accelerating cavity 15 is controlled to be increased or decreased. When the charged particle beam is extracted under such timing control, the acceleration radio frequency voltage is applied in the same manner as with the prior art. After the spot dose value has exceeded the prescribed dose, the amplitude value of the acceleration radio frequency voltage starts to be increased. When the spot dose has reached the target dose, the voltage is kept constant. By the time the irradiation is restarted, the acceleration radio frequency voltage is controlled to start reducing the amplitude value of the acceleration radio frequency voltage. As a result, an extra irradiation beam 10*e*1 shown in FIG. 2(*c*) is made significantly smaller than the extra irradiation beam 10*e*2 of the prior art illustrated in FIG. 5(*d*). In this manner, the extra dose can be reduced.

As described, the amplitude value of the radio frequency voltage applied to the accelerating cavity 15 is changed between the time the beam is extracted from the synchrotron 13 and the time beam extraction is stopped. Before the beam extraction is stopped (turned off), the amplitude value of the radio frequency voltage applied to the accelerating cavity is raised so as to increase the synchrotron oscillation frequency at the time of beam deactivation. This in turn shortens the charged particle beam stop time. And before the beam extraction is started (turned on), the acceleration radio frequency voltage is lowered so as to suppress the momentum dispersion (range fluctuations) at the time of beam extraction. This contributes to inhibiting the dose of the charged particle beam deviating from the target value.

The invention is not limited to the aforementioned embodiment and may be variously modified and changed and is applicable to the modifications and changes. The embodiment is described in detail in order to clarify the invention and is not necessarily limited to the devices having all the configurations described above.

What is claimed is:

1. A charged particle beam irradiation system comprising:
a charged particle beam generator including a charged particle beam injector;
a synchrotron in the charged particle beam generator which accelerates the charged particle beam received from the charged particle beam injector and extracts the accelerated charged particle beam from the synchrotron;
an irradiation device, including a scanning magnet that deflects the charged particle beam to scan an irradiation target with the charged particle beam extracted from the synchrotron and to irradiate the irradiation target;
a beam transportation system which connects the charged particle beam generator with the irradiation device and which transports the charged particle beam from the synchrotron to the irradiation device; and
a control system for the synchrotron, the beam transportation system, and the irradiation device;
wherein the synchrotron has an accelerating cavity to accelerate the charged particle beam, using a radio frequency acceleration voltage, up to a predetermined energy level; and
wherein the control system includes an acceleration radio frequency controller that controls a charged particle beam acceleration radio frequency voltage applied to the accelerating cavity, the charged particle beam acceleration radio frequency controller operating to increase an amplitude value of the charged particle beam acceleration radio frequency voltage applied to the accelerating cavity, when irradiation of a selected irradiation spot by an irradiation dose of the charged particle beam has reached a prescribed dose, to maintain the amplitude value of the charged particle beam acceleration radio frequency value after irradiation of the selected irradiation spot has been completed and to reduce the increased amplitude value of the charged particle beam acceleration radio frequency voltage when irradiation of one of the selected irradiation spot and a different irradiation spot, with the charged particle beam, is restarted.

2. The charged particle beam irradiation system according to claim 1,
wherein the acceleration radio frequency controller determines the irradiation dose based on a time required to increase the amplitude value of the charged particle beam acceleration radio frequency voltage when the irradiation dose has reached a target dose.

3. An operating method for a charged particle beam irradiation system including a charged particle beam generator having a charged particle beam injector and including a synchrotron to accelerate the charged particle beam received from the charged particle beam injector and to extract the accelerated charged particle beam from the synchrotron, an irradiation device including a scanning magnet that deflects the charged particle beam to irradiate an irradiation target having at least first and second irradiation spots with the charged particle beam extracted from the synchrotron, a beam transportation system which connects the charged particle beam generator with the irradiation device and which transports the charged particle beam from the synchrotron to the irradiation device, and a control system for the synchrotron, the beam transportation system, and the irradiation device, the operating method comprising:
at a start of irradiation of a first irradiation spot with the charged particle beam, setting to a first amplitude level an amplitude value of the charged particle beam acceleration radio frequency voltage applied to an accelerating cavity of the synchrotron when the charged particle beam is extracted from the synchrotron;

increasing the amplitude value of the charged particle beam acceleration radio frequency voltage from a first amplitude value to a second amplitude value when an irradiation dose of the charged particle beam delivered to the first irradiation spot reaches a prescribed dose; and reducing the amplitude value of the charged particle beam acceleration radio frequency voltage from the second amplitude to the first amplitude when irradiation with the charged particle beam of the first irradiation spot is stopped and before irradiation of the second irradiation spot is started.

4. The operating method for the charged particle beam irradiation system according to claim 3, further comprising determining the prescribed dose based on a time required to increase the amplitude value of the charged particle beam acceleration radio frequency voltage when the irradiation dose reaches a target dose.

5. The operating method for the charged particle beam irradiation system according to claim 4, further comprising increasing the amplitude value of the charged particle beam acceleration radio frequency voltage up to the second amplitude value when the irradiation dose reaches the target dose.

* * * * *